United States Patent
Boese et al.

(10) Patent No.: US 7,630,751 B2
(45) Date of Patent: Dec. 8, 2009

(54) METHOD AND MEDICAL IMAGING SYSTEM FOR COMPENSATING FOR PATIENT MOTION

(75) Inventors: Jan Boese, Eckental (DE); Benno Heigl, Coburg (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 418 days.

(21) Appl. No.: 11/045,653

(22) Filed: Jan. 28, 2005

(65) Prior Publication Data

US 2005/0203373 A1 Sep. 15, 2005

(30) Foreign Application Priority Data

Jan. 29, 2004 (DE) ............... 10 2004 004 603

(51) Int. Cl.
*A61B 5/05* (2006.01)
(52) U.S. Cl. ................... 600/407; 600/425
(58) Field of Classification Search ............ 600/407, 600/425; 378/68, 107
See application file for complete search history.

(56) References Cited

U.S. PATENT DOCUMENTS

| | | | |
|---|---|---|---|
| 2,534,623 A * | 12/1950 | Pitts et al. ............... | 5/601 |
| 4,870,692 A | 9/1989 | Zuiderveld et al. | |
| 5,647,360 A * | 7/1997 | Bani-Hashemi et al. ..... | 600/425 |
| 6,084,590 A * | 7/2000 | Robotham et al. .......... | 345/419 |
| 6,118,845 A * | 9/2000 | Simon et al. ............... | 378/62 |
| 6,516,046 B1 * | 2/2003 | Frohlich et al. ............. | 378/65 |
| 6,594,378 B1 * | 7/2003 | Li et al. .................... | 382/128 |
| 6,628,977 B2 * | 9/2003 | Graumann et al. .......... | 600/407 |
| 2001/0002830 A1 * | 6/2001 | Rahn et al. ................. | 345/158 |
| 2002/0085668 A1 | 7/2002 | Blumhofer et al. | |

(Continued)

FOREIGN PATENT DOCUMENTS

DE 100 51 370 A1 5/2002

(Continued)

OTHER PUBLICATIONS

Hemmendorff et al.; "Motion-compensated digital subraction angiography"; SPIE '99, San Diego USA, Proceedings of SPIE's International Symposium on Medical Imaging 1999, vol. 3661, Image Processing, Feb. 1999, pp. 1396-1405; Magazine; 1999.

(Continued)

*Primary Examiner*—Eric F Winakur
*Assistant Examiner*—Helene Bor

(57) ABSTRACT

Disclosed herein is a method, and system (1) for implementing same, to compensate for patient motion in series recordings in medical imaging, in which a plurality of images of an examination area of a patient (17) are recorded at time intervals with an imaging system (1) and related to each other. Before the start of the series recordings a 3D image data set is recorded by a 3D recording of the examination area, which establishes a reference system. A first spatial position of the examination area in the reference system is obtained by recording a first image of the series recordings and then registering it or by calculating it. Each further image of the series recordings is registered immediately after recording to obtain the current spatial position of the examination area. Differences in spatial position are compensated for at least approximately by changing geometric relationships of the imaging system (1).

16 Claims, 2 Drawing Sheets

U.S. PATENT DOCUMENTS

| | | | |
|---|---|---|---|
| 2003/0083562 A1 | 5/2003 | Bani-Hashemi et al. | |
| 2003/0125622 A1* | 7/2003 | Schweikard et al. | 600/437 |
| 2003/0191394 A1 | 10/2003 | Simon et al. | |
| 2006/0183999 A1* | 8/2006 | Lorenz et al. | 600/410 |
| 2006/0241443 A1* | 10/2006 | Whitmore et al. | 600/439 |
| 2006/0253031 A1* | 11/2006 | Altmann et al. | 600/466 |

FOREIGN PATENT DOCUMENTS

DE    102 50 655 A1    6/2003

OTHER PUBLICATIONS

Meijering et al.; "Reduction of patient motion artifacts in digital subtraction angiography: evaluation of a fast and fully automatic technique"; Radiology, Apr. 2001; 219(1): pp. 288-293; Magazine; 2001.

Meijering et al.; "Retrospective Motion Correction in Digital Subtraction Angiography: A Review"; IEEE Transactions on Medical Imaging, vol. 18, No. 1, Jan. 1999, pp. 2-21; Magazine; 1999.

Weese et al.; "2D/3D Registration and Motion Tracking for Surgical Interventions"; Philips Journal of Research vol. 51, No. 2, (1998), pp. 299-316; Magazine; 1998.

Penney et al.; "Validation of a two- to three-dimensional registration algorithm for aligning preoperative CT images and intraoperative fluoroscopy images"; Med. Phys. 28 (6), Jun. 2001, pp. 1024-1032; Magazine; 2001.

* cited by examiner

METHOD AND MEDICAL IMAGING SYSTEM FOR COMPENSATING FOR PATIENT MOTION

CROSS REFERENCE TO RELATED APPLICATIONS

This application claims priority to the German application No. 10 2004 004 603.4, filed Jan. 29, 2004 which is incorporated by reference herein in its entirety.

FIELD OF INVENTION

The present invention relates to a method to compensate for patient motion in series recordings in medical imaging, with which a plurality of images of an examination area of a patient are recorded at time intervals using an imaging system and related to each other, in particular to compensate for motion in the case of digital subtraction angiography or the pathfinder technique. The invention also relates to an imaging system with a radiation source, detector and patient table as well as a control, image processing and image display unit, which is configured to implement the method.

BACKGROUND OF INVENTION

In one of the main fields of application of the present method, namely the field of digital subtraction angiography, blood vessels in the human body are captured and displayed using the imaging system, in this instance an X-ray unit. With this method series of X-ray images of the relevant examination area of the patient are recorded, while a contrast agent is injected to highlight the vessels (fill images). An image of the examination area is also recorded without injection of a contrast agent (mask image). By digitally subtracting the mask image from the respective fill images subtraction images are obtained, on which only the vessels can be identified, while subtraction causes other X-ray-absorbent structures, e.g. bones, superimposed thereon to disappear.

Image subtraction primarily assumes that the images in question were recorded under the same geometric conditions, so that they are congruent. Motion of the mapped structures between the individual recordings can lead to interference from motion artifacts in the subtracted images. These can be caused by motion of the patient between the recording of the mask image and the recording of the fill images. One consequence of such motion can be that the resulting subtraction image can no longer be used for diagnosis. In practice this can mean therefore that subtraction images subject to interference from such motion artifacts have to be repeated. This is associated with additional outlay of time and contrast agents and additional exposure of the patient to radiation.

One method used with digital subtraction angiography is the so-called pathfinder technique, also referred to as road mapping. This technique is used for the selective catheterization of vessels during interventional therapy. During such vascular interventions the current position of an X-ray-absorbent catheter is displayed by means of fluoroscopy in a two-dimensional image. In order also to be able to identify the blood vessel as a so-called road map, at the start of the intervention an image is recorded, in which a small quantity of contrast agent has been injected. This image is used as the mask image. The subsequent fluoroscopy images obtained without injecting a contrast agent are each subtracted from the mask image. This produces subtraction images, in which the catheter can be identified as a light from against the dark blood vessel and the background has been eliminated by subtraction.

Road mapping is also subject to interference due to motion of the mapped structures during series recordings in a similar manner to digital subtraction angiography. Motion between the recording of the mask image and the respective fluoroscopy image gives rise to two problems here. On the one hand the background is no longer correctly subtracted, so image artifacts result. On the other hand it can happen that the position of the catheter in relation to the displayed blood vessel, as determined by means of the image, is not correct. This serious error can for example result in the catheter being shown outside the vessel in the image, even though it is actually inside the vessel. In extreme cases such false representations can lead to errors in catheter control and cause damage to the vessel. If the patient moves during the intervention, the road map therefore frequently has to be refreshed by a repeat recording of a mask image. This requires additional time outlay and contrast agent consumption and is associated with a higher radiation dose for the patient.

Various solutions are currently known to avoid or alleviate this problem. Essentially there are 3 different approaches.

Patient-related solutions have the aim of preventing patient motion during recording. Thus in the case of thoracic examinations for example the patient is trained to hold their breath during series recordings. A further option is that of preventing some sources of motion artifacts by general anesthesia. One disadvantage of the patient-related method is that it is either only partially effective or it cannot always be used. General anesthesia is for example associated with a number of risks and is there fore not medically indicated for many applications of digital subtraction angiography. On the other hand even with general anesthesia some sources of motion artifacts remain, e.g. respiratory motion.

In the case of solutions relating to imaging recording, image recording is implemented such that motion artifacts are minimized. To date so-called gating methods have primarily been known for this purpose, with which recording is linked to physiological measurement. For example in the case of ECG gating, images are only acquired in a specific cardiac phase, so that heart motion is compensated for. Gating methods can however only be used for a few specific applications and can only prevent motion artifacts caused by specific sources, for which physiological signals can be measured.

A further approach to reducing motion artifacts involves retrospective image processing of the recorded images. These techniques aim to obtain a better correspondence of the mask image and the fill image by appropriate image processing. The simplest technique used is so-called pixel shifting or subpixel shifting, in which the user shifts the mask image toward the fill image manually in two dimensions, until minimization of the motion artifacts in the subtraction image is achieved. This method is implemented in all commercial angiography systems. Also automatic methods, which establish the best correspondence based on quantifiable similarity measures, are present in some commercial angiography systems. More complex methods do not use overall pixel shifting over the entire image area but optimize local areas of the image separately from each other, as disclosed for example in U.S. Pat. No. 4,870,692 A. Also numerous more complex methods for motion correction are proposed in the scientific literature. These are essentially optimization methods, in which the aim is to find the transformation between mask image and fill image, which produces the fewest motion artifacts. Further examples of retrospective image processing can be found in the publications "Motion-compensated digital subtraction angiography", Magnus Hemmendorff et al., SPIE '99, San Diego USA, Proceedings of SPIE's International Symposium on Medical Imaging 1999, Volume 3661, Image Processing, February 1999, pp. 1396-1405; Meijering E. H. et al., "Reduction of patient motion artefacts in digital subtraction angiography: evaluation of a fast and fully automatic technique", Radiology, 2001 April, 219(1): 288-293; or "Retrospective Motion Correction in Digital Subtraction Angiography: A Review", Erik H. W. Meijering et al., IEEE Transactions on Medical Imaging, Vol. 18, No. 1, January 1999, pp. 2-21.

Retrospective image processing can however only compensate approximately for motion. Arbitrary motion cannot be corrected. Even with a restriction to a correction of 6 degrees of freedom corresponding to the rotation and translation of a rigid element, it is not possible to determine motion uniquely from the two-dimensional images. The complex image processing methods also require a great deal of computation time and cannot therefore easily be implemented in real time. Manual image processing methods (pixel shifting) require user interaction and can take a lot of time. They can also essentially only be used for subsequent improvement of DSA images, as with road mapping there is little time for interaction.

DE 100 51 370 A1 covers a method for the precise positioning of a patient in radiotherapy or radiosurgery. In this field a computer tomograph is used to generate a three-dimensional image data set of the examination area, on the basis of which subsequent radiotherapy, for example the irradiation of a tumor, is planned. The patient then has to be positioned as precisely as possible in relation to the linear accelerator required for radiotherapy, so that irradiation takes place as exactly as possible at the planned position. With this publication the most precise positioning possible is achieved by recording X-ray fluoroscopy images from two different directions at the linear accelerator, which are then use d to determine the correspondence of position or difference in position by comparison with correspondingly reconstructed (virtual) fluoroscopy images from the previously generated 3D image data set. The position of the patient can then be adjusted to compensate for this position difference by moving the patient table. The patient is pre-positioned by means of a computer and camera controlled navigation and tracking system with the assistance of synthetic markers on the patient.

Like DE 100 51 370 A1, DE 102 50 655 A1 discloses a patient positioning system for the same purpose. To solve the positioning problem, in this publication a surface image generator is used both at the CT device and at the linear accelerator, the images of which are compared and used to position the patient precisely.

SUMMARY OF INVENTION

Based on this prior art, an object of the present invention is to specify a method and an associated imaging system to compensate for patient motion in series recordings in medical imaging, with which patient motion can be compensated for during image recording without time-consuming user interaction, the method being such that it can be implemented in real time. The method and the associated imaging system are intended in particular to improve image results for digital subtraction angiography and road mapping with the smallest possible time outlay for the operator.

The object is achieved by the claims. Advantageous embodiments of the method and imaging system are set out in the dependent claims or will emerge from the description which follows and the exemplary embodiments.

With the present method to compensate for patient motion in series recordings in medical imaging, with which a plurality of images of an examination area of a patient are recorded at time intervals using an imaging system and related to each other, before the start of the series recordings a 3D recording of the examination area is used to record a 3D image data set, which establishes a reference system. This can either take place beforehand with a different 3D imaging modality—in the case of X-ray series recordings with a C-arm device for example by CT, MR or 3D angiography—or with the same imaging system, as is used for the series recordings. The first spatial position of the examination area in the reference system is then obtained either by recording a first image of the series recordings and registering it with the 3D image data set or it is calculated from a known calibration of the imaging system. The latter is only possible when recording the 3D image data set with the same imaging system. Each further image of the series recordings is then registered immediately after recording with the 3D image data set, to obtain the current spatial position of the examination area in the reference system. Any difference between this current spatial position and the first spatial position is determined and at least some of the difference is compensated for at least approximately by changing geometric relationships of the imaging system in temporal proximity to registration, preferably in real time.

The method therefore uses the technique of registration, in particular 2D/3D registration, to determine changes in the position of the patient or examination area, i.e. changes in the position and orientation of this examination area, during implantation of the series recordings. Based on the differences determined, patient motion is then compensated for at least partially by controlling the geometric relationships of the imaging system, preferably by real time control. Compensation can thereby be effected completely by this change in the geometric relationships, depending on the activated components of the imaging system. Individual degrees of freedom can however also be compensated for by adjustment, in particular rotation or translation, of the image content of the respective image, in which the difference was determined. In this way individual images of the series recordings are obtained, which show the examination area in each instance in the approximately identical position and orientation. When simply compensating for motion of the patient or examination area by changing the geometric relationships of the imaging system, the adjustable components of the imaging system are controlled such that the relative relationship between the examination area to be mapped and the recording system remains approximately constant during implementation of the series recordings.

Appropriate techniques for registration, in particular 2D/3D registration, are known to the person skilled in the art. These include in particular image-based methods, which establish a link between the coordinates systems of the 3D data set and the respective 2D image data set. Examples of 2D/3D registration can for example be found in the publications by J. Weese et al., "2D/3D Registration and Motion Tracking for Surgical Interventions", Philips Journal of Research 51 (1998), 299-316, and by G. P. Penney et al., "Validation of a two- to three-dimensional registration algorithm for aligning preoperative CT images and intraoperative fluoroscopy images", Med. Phys. 28 (6), June 2001, 1024-1032.

The present method can be used in particular for motion compensation in digital subtraction angiography or with the pathfinder technique, to obtain the most congruent individual images possible for subtraction. With the method therefore motion of the patient or the examination area of the patient under observation is already compensated for during image recording by real time control of the geometric relationships of the imaging system, in some instances in combination with geometric adjustment of the image content.

Unlike most previously known methods for motion correction, the present method does not require interaction with the operator. The previous methods for retrospective image processing can operate in principle only approximately. Major motion can barely be corrected with these methods and minor motion only approximately. The proposed method operates with great precision in particular even with major motion, so that the need for multiple recording of a mask image is dispensed with. This saves time and contrast agent and reduces the X-ray dose in the case of X-ray recordings. The present method also allows sedation or anesthesia of the patient just for the purposes of minimizing motion artifacts to be dispensed with in certain cases.

Different components of the imaging system can be used to compensate for differences due to patient motion by adjusting the geometric relationships of the imaging system. Such adjustment is preferably achieved by a translation and/or rotation of the patient table in 1-3 degrees of freedom. The patient table can already be moved by motor at least in the 3 degrees of freedom of translation in the case of C-arm devices for angiography applications.

The differences can also be adjusted by rotating the C-arm in the RAO/LAO or cranial/caudal direction in 2 degrees of freedom. In a further embodiment a detector is used, which can be rotated in 1-3 degrees of freedom, so that certain differences can be compensated for by moving the detector.

To compensate for the differences detected, it is also possible to change the image content of the recorded images geometrically. This relates in particular to a rotation of the image content about an axis perpendicular to the image plane and translation in the two degrees of freedom of translation of the two-dimensional image recording. It is also possible to scale the image. Depending on the type of patient motion a combination of the two compensation techniques, i.e. changing the geometric relationships of the imaging system and geometric adjustment of the image content, can be advantageous.

Naturally with the present method retrospective image processing methods can also be used after the at least approximate compensation for motion, to improve the image results still further. Approximate compensation by changing the geometric relationships of the imaging system can thereby be used to compensate for gross motion, while minor residual errors are eliminated by retrospective image processing.

The present imaging system comprises at least a radiation source and a detector, a patient table, a control unit, an imaging processing and image display unit. The geometric relationships for image recording can be changed by motor-controlled movement of the patient table and the image recording unit, comprising radiation source with detector opposite. The imaging system is characterized in that a compensation unit is provided, which registers every recorded image of a patient in real time immediately after recording with a stored 3D image data set, uses said registration to determine interim motion of the patient and uses the control unit to activate one or a plurality of components, the position of which can be changed to change the geometric relationships of the imaging system, such that at least some of the patient motion determined is compensated for at least approximately. The imaging system is hereby preferably configured in the form of a C-arm device, with the positions of the patient table and C-arm preferably being changed to represent the movable components.

BRIEF DESCRIPTION OF THE DRAWINGS

The present method and the associated imaging system are described in more detail below with reference to an exemplary embodiment in conjunction with the drawing, in which.

DETAILED DESCRIPTION OF INVENTION

The present method is described below with reference to an X-ray angiography unit for neuroradiology applications. The method can of course also be used in other fields, in which digital subtraction angiography and/or road mapping are used. The present method can also be used with other techniques for medical imaging, in which series recordings have to be taken and related to each other.

In the example below the embodiments are restricted to the instance of the correction of head motion of a patient. As the head can be considered approximately to be a rigid element, the motion correction is restricted to the six degrees of freedom of translation and rotation of a rigid element in the three-dimensional space.

Figure 1:
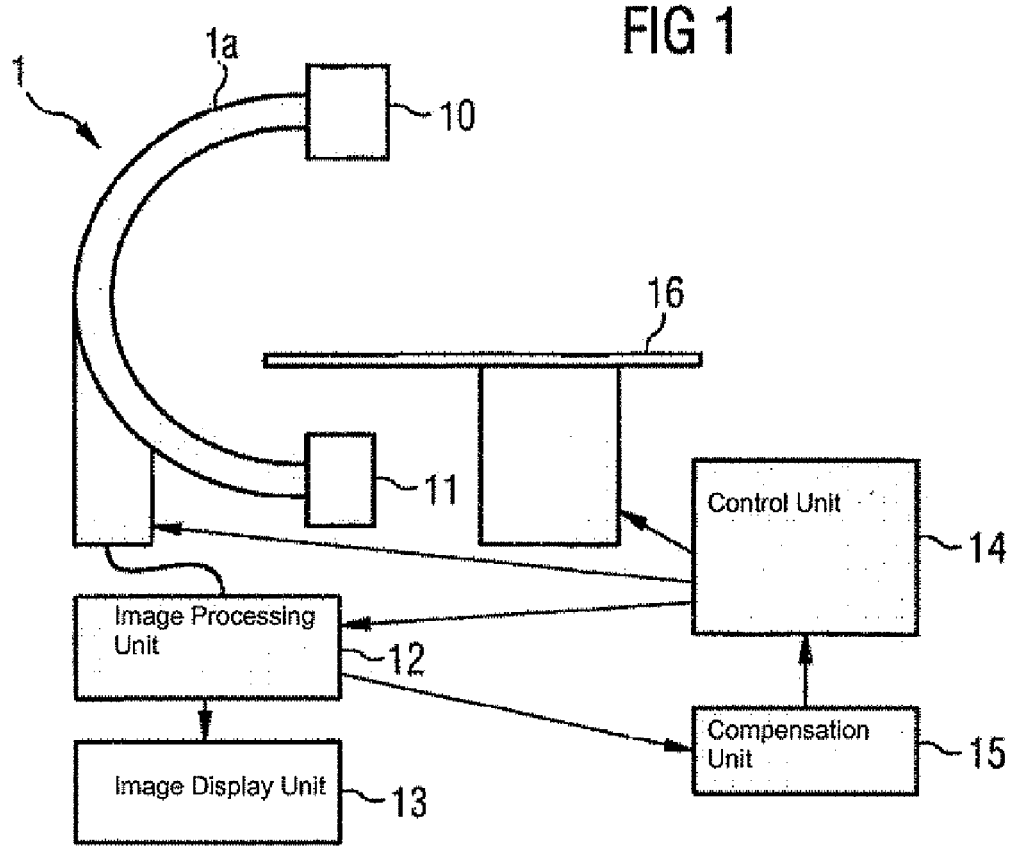
FIG. 1 shows an example of a C-arm device as the imaging system to implement the present method.

A neuroradiology X-ray angiography unit 1 is used for image recording, as shown schematically in FIG. 1. The X-ray angiography unit 1 includes a C-arm 1a that can be rotated about two axes, to which an X-ray tube 10 and a detector 11 opposite the X-ray tube are attached, an image processing unit 12 and an image display unit 13. This unit also comprises the patient table 16, which can be adjusted by motor in the three degrees of freedom of translation (height, side, length), a control unit 14 to control image recording and the compensation unit 15. By rotating the C-arm 1a it is possible to record different projections of the examination area of the patient lying on the patient table 16 during the examination as two-dimensional images. The X-ray angiography system 1 shown is also able to implement rotation angiography recordings and generate 3D images.

Figure 2:
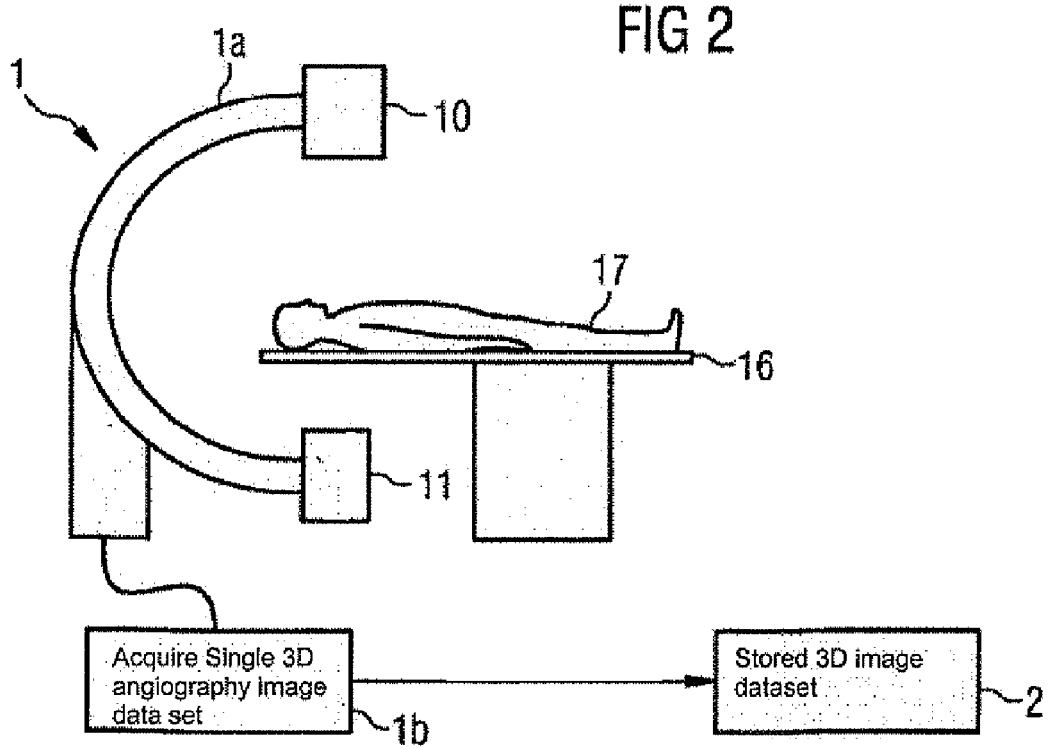
FIG. 2 shows an example of the recording of a 3D image data set when implementing the present method.

FIG. 2 shows an example of the first method steps during the implementation of the present method using the X-ray angiography system 1. Before implementing the digital subtraction angiography or recording the roadmap recordings a single 3D angiography image data set of the examination area of the patient (17) is acquired (1b) and stored (stored 3D image data set 2).

Figure 3:
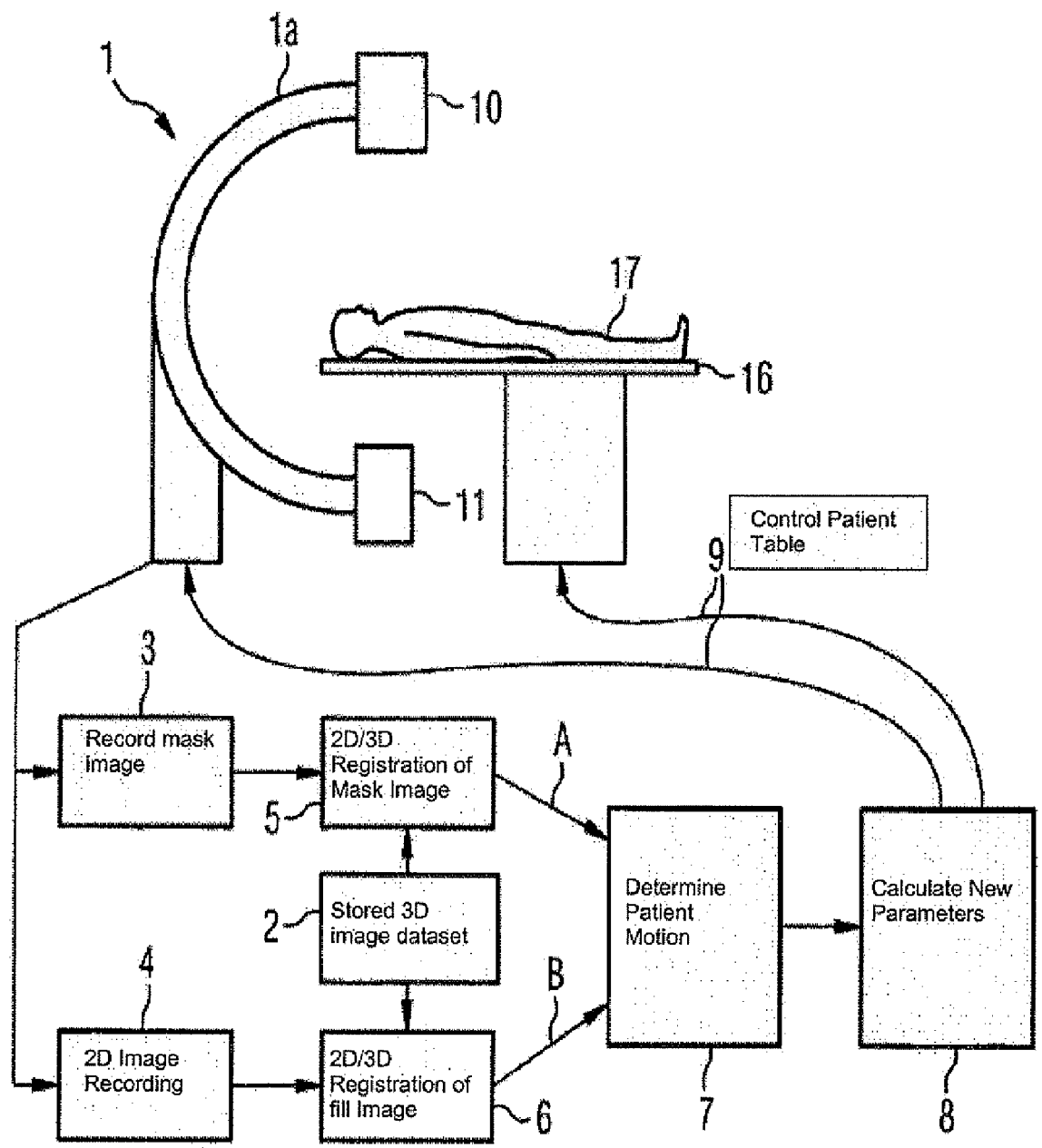
FIG. 3 shows an example of compensation for patient motion during implementation of the series recordings.

At the start of the series recordings immediately after the mask image has been recorded (step 3), a 2D/3D registration 5 of the mask image is implemented with the previously recorded and stored 3D image data set 2 (FIG. 3). As a result of this registration, a transformation A is obtained, which represents the position of the head of the patient in the reference system of the stored 3D image data set 2.

The further images or so-called fill images are also registered continuously after the 2D image recording 4 with the 3D image data set 2 by a 2D/3D registration 6. Each of these registrations produces a transformation B. The difference between transformation A and transformation B is used in step 7 to determine patient motion. This is done immediately after the recording of each 2D image in real time. The difference between the two transformations, which corresponds to the change in position of the head, is also used in real time to calculate 8 the new recording parameters and image processing parameters, to minimize the differences between the transformations A and B in a control loop. By controlling 9 the patient table 16, the C-arm 1a and image processing, the recording geometry and image processing are adjusted such that patient motion is essentially compensated for.

In the present example the recording parameters are changed by activating the patient table 16 in the three degrees of freedom of translation and the C-arm 1a in the two degrees of freedom of rotation. The remaining degree of freedom of rotation is achieved via image processing by rotating the image content about an axis perpendicular to the image plane. As well as controlling these components, the recording geometry can also be achieved in an angiography system for example by rotating the patient table 16 in one to three degrees of freedom of rotation or by rotating the detector in one to three degrees of freedom of rotation. It is also possible to shift or scale the image content in two degrees of freedom of translation.

In the present example the transformations A and B describe the registration between a 2D and a 3D coordinates system and generally contain 11 parameters, 6 for rotation and translation of the 3D image data set and 5 for the projection geometry of the unit 1. If the C-arm 1a moves in a reproducible manner, the projection geometry can be determined by calibration, so that only six degrees of freedom are determined by the 2D/3D registration.

Naturally the compensation for patient motion shown in the present example can also be combined with a retrospective image processing method. In this manner it is possible to compensate for gross motion by means of the described tracking of the recording system, while residual minor errors are eliminated by retrospective image processing.

The invention claimed is:

1. A method of compensating for patient motion when recording a series of medical images useful in conjunction with a digital subtraction angiography or a pathfinding technique, wherein the medical images of an examination area of a patient are recorded at specific time intervals using an imaging system and are correlated with each other, the method comprising:
    recording a three-dimensional image data set of the examination area, the three-dimensional image data set defining a frame of reference;
    recording a first 2D image of the examination area;
    determining a first spatial position of the examination area relative to the frame of reference by registering said first 2D image with said three-dimensional image data set;
    recording further 2D medical images of the series and registering each further recorded 2D medical image with the three-dimensional image data set immediately after its recording for determining a current spatial position of the examination area relative to the frame of reference;
    determining a difference between the current and the first spatial positions; and
    compensating for the difference by adjusting at least one geometrical proportion of the imaging system
    wherein the recording further 2D medical images and compensating for the difference is conducted continuously and in real time;
    wherein the geometrical proportion is adjusted immediately after registering the recorded medical image with the three-dimensional image data set; and
    wherein adjusting the geometrical portion includes a translation of a patient table of the imaging system, the translation comprising one, two or three degrees of freedom and/or a rotation of the patient table, the rotation comprising one, two or three degrees of freedom.

2. The method according to claim 1, wherein the first spatial position of the examination area is determined by recording a first medical image of the series and registering the first medical image with the three-dimensional image data set.

3. The method according to claim 1, wherein the first spatial position of the examination area is calculated using a known calibration of the imaging system.

4. The method according to claim 1, wherein the three-dimensional image data set and the medical images of the series are recorded by the same imaging system.

5. The method according to claim 1, wherein a remaining difference between the current and the first spatial positions is compensated for by processing the further medical images.

6. The method according to claims 1, wherein adjusting the geometrical portion includes a rotation of an image recording detector.

7. The method according to claim 6, wherein the rotation of the detector includes one, two or three degrees of freedom.

8. The method according to claims 1, wherein the imaging system includes a C-arm device and adjusting the geometrical portion includes a rotation of the C-arm.

9. The method according to claim 8, wherein the rotation of the C-arm includes one, two or three degrees of freedom.

10. The method according to claim 5, wherein processing the further medical images includes a translation of an image content.

11. The method according to claim 1, wherein the translation includes one, two or three degrees of freedom.

12. The method according to claim 1, wherein processing the further medical images includes scaling of an image content.

13. The method according to claim 1, wherein a remaining difference between the current and the first spatial positions is compensated for by utilizing a retrospective image processing method.

14. An imaging system useful in conjunction use with a digital subtraction angiography or a pathfinding technique, the imaging system comprising:
    at least one radiation source;
    a radiation detector;
    a patient table adjustable by a motor operatively connected to the patient table the translation includes one, two or three degrees of freedom;
    a control unit for controlling image recording;
    an image processing unit;
    an image display unit, wherein the radiation source, the radiation detector and the patient table are adjustable components and the mutual positioning of which relative to each other defines the geometrical proportions of the imaging system; and
    a compensation unit configured for:
        registering a first recorded 2D image with a stored three-dimensional image data set to determine a first spatial position and registering a series of recorded 2D images with the three-dimensional image data set to determine a current spatial position, each registering of a recorded 2D medical image of a patient with the stored three-dimensional image data set being conducted continuously and in real time immediately after recording the respective medical image;
        determining an interim motion of the patient using the registration; and activating at least one of the adjustable components for adjusting at least one geometrical proportion of the imaging system using the control unit, so that the determined interim motion of the patient is compensated for continuously and in real-time;

wherein the geometrical proportion is adjusted immediately after registering the recorded medical image with the three-dimensional image data set; and wherein adjusting the geometrical portion includes a translation of a patient table of the imaging system, the translation comprising one, two or three degrees of freedom and/or a rotation of the patient table, the rotation comprising one, two or three degrees of freedom.

15. Imaging system according to claim 14, wherein the compensation unit is adapted to activate the image processing unit for processing at least one geometrical proportion of an image content of a current medical image, so that a remaining uncompensated interim motion of the patient is compensated for.

16. The imaging system according to claim 14, wherein the imaging system is an X-ray system having a C-arm device.

* * * * *

UNITED STATES PATENT AND TRADEMARK OFFICE
CERTIFICATE OF CORRECTION

PATENT NO.         : 7,630,751 B2                                       Page 1 of 1
APPLICATION NO. : 11/045653
DATED              : December 8, 2009
INVENTOR(S)        : Boese et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 630 days.

Signed and Sealed this

Second Day of November, 2010

David J. Kappos
*Director of the United States Patent and Trademark Office*